United States Patent [19]

Suda et al.

[11] Patent Number: 5,078,710
[45] Date of Patent: Jan. 7, 1992

[54] SURFACE MATERIAL FOR SANITARY ARTICLES

[75] Inventors: Yasunori Suda; Takatoshi Kobayashi, both of Utsunomiya; Akira Yamanoi, Ichikai, all of Japan; Tamio Yasuno, Singapore, Singapore; Daisuke Shiba, Utsunomiya, Japan

[73] Assignee: Kao Corporation, Tokyo, Japan

[21] Appl. No.: 494,832

[22] Filed: Mar. 16, 1990

Related U.S. Application Data

[63] Continuation of Ser. No. 224,706, Jul. 27, 1988, abandoned.

[30] Foreign Application Priority Data

Jul. 30, 1987 [JP] Japan ................ 62-191332
Sep. 14, 1987 [JP] Japan ................ 62-230495
Oct. 30, 1987 [JP] Japan ................ 62-275220
Dec. 16, 1987 [JP] Japan ................ 62-318333
Feb. 10, 1988 [JP] Japan ................ 63-29159

[51] Int. Cl.$^5$ ............................................. A61F 13/15
[52] U.S. Cl. ................ 604/383; 604/366; 604/382; 428/137; 428/87
[58] Field of Search ............... 604/383, 380-384, 604/385.1, 366, 370; 428/137, 87

[56] References Cited

U.S. PATENT DOCUMENTS 3,929,135 12/1975 Thompson .
3,945,386  3/1976 Anczurowski et al. ......... 604/383
4,324,246  4/1982 Mullane et al. .
4,535,020  8/1985 Thomas et al. ............... 604/383
4,626,254 12/1986 Windlund et al. ............ 604/383
4,634,440  1/1987 Widlund et al. .............. 604/383
4,710,186 12/1987 DeRossett et al. ........... 604/383
4,798,604  1/1989 Carter ........................ 604/383

FOREIGN PATENT DOCUMENTS

57-1340   1/1982 Japan .
57-17081  4/1982 Japan .
58-180602 10/1983 Japan .
2085305   4/1982 United Kingdom ........... 604/390

Primary Examiner—C. Fred Rosenbaum
Assistant Examiner—Mark O. Polutta
Attorney, Agent, or Firm—Birch, Stewart, Kolasch & Birch

[57] ABSTRACT

A sanitary article comprises an absorbent and a sheet of a surface material to envelop the absorbent, the sheet comprising an opaque, hydrophobic film, having recesses in its land portion, the recesses being formed to have a bottom and side walls, the side walls having a slanting part, the slanting part being provided therein with an opening so that the slanting part having the opening may not be covered with the land portion.

10 Claims, 3 Drawing Sheets

SURFACE MATERIAL FOR SANITARY ARTICLES

This application is a continuation of application Ser. No. 07/224,706 filed on July 27, 1988, now abandoned.

The present invention relates to a surface material suitable for use in sanitary articles such as disposable absorbent articles More particularly, this invention is concerned with a surface material comprising a shaped film having openings and suitable for use in sanitary articles such as sanitary napkins and similar articles

PRIOR ART

It is well known that absorbent articles used for absorbing and retaining a liquid excreted from a human body have a structure comprising a liquid-permeable surface material, a liquid-impermeable and leak-proof back sheet, and an absorbent disposed therebetween for absorbing and retaining the liquid. The liquid-permeable surface material (also called a "top sheet" or a "cover stock") used in such absorbent articles is required to permit a liquid to be effectively and freely transferred into an absorbent, to prevent the liquid transferred into the absorbent from returning, thereby giving a feeling of dryness to the human body, and to be agreeable to the touch when it is in contact with the surface of a human body.

To attain this objective, many proposals have been made and so are also improved techniques. For example, a typical technique comprises using as the surface material a nonwoven fabric, i.e., an assembly of fine hydrophobic fibers, so as to provide a clearance of a hydrophobic atmosphere between the human body and the absorbent, thereby not adversely affecting permeation of a fluid and relieving fluid return from an absorbent whereby a substantially dry surface is provided (see Japanese Patent Laid-Open No. 18060/1983). Another typical technique comprises providing a hydrophobic and liquid-impermeable film with openings, thereby further relieving liquid return from an absorbent (see Japanese Patent Publication No. 17081/1982 and Japanese Patent Laid-Open No. 1340/1982).

However, in these techniques, use of a nonwoven fabric of hydrophobic material has a drawback in that the liquid to be transferred into an absorbent tends to be retained in the minute space inevitably formed in the fiber assembly and that upon application of pressure, the retained liquid is readily transferred toward the surface of the human body. Especially, in the case of a colored liquid, such as menstrual blood, it exhibits a grave visual defect.

In the meantime, it has been proposed to provide a liquid-impermeable film with a particular opening, thereby decreased liquid retention in the surface material so as not to adversely affect the essential functions of the surface material. However, due to the hydrophobic property of the film, the opening area must be large enough to ensure free passage of a liquid. Further, due to the loss of the hydrophobic property within the opening, prevention of the return on the liquid in the opposite direction is not always successful. In the case of the absorption of a colored liquid, the liquid is observable through the opening. Therefore, this surface material is not always desirable.

Consequently, early development of a surface material permitting free passage of a fluid into an absorbent, preventing the fluid from returning and capable of covering the color of the liquid absorbed in the case of the absorption of a colored liquid has been desired in the art.

SUMMARY OF THE INVENTION

A sanitary article of the invention comprises an absorbent and a sheet of a surface material to envelop the absorbent, the sheet comprising an opaque, hydrophobic film, having recesses in its land portion, which is also called a top section, the recesses being formed to have a bottom portion and side walls, the side walls having a slanting part, the slanting part being provided therein with an opening so that the slanting part having the opening may not be covered with the land portion. The opening is always exposed to sight when it is looked down upon.

It is preferable that the opening has a size of 0.02 to 30 square mm and the number of openings ranges from 1 to 100 per one square cm of the sheet. An angle formed between the land portion and the slanting part of the side walls is preferred to range from 20° to less than a right angle.

In addition, the invention includes the following five preferable embodiments (1) to (5).

(1) The sheet comprises the opaque, hydrophobic film and a layer of fibrous aggregates, lined on the film on the side which contact the skin of a user.

(2) The sheet comprises the opaque, hydrophobic film and a layer of fibrous aggregates lined on the film on the side nearer to the absorbent.

(3) The bottom portion is formed to be upwardly convex or toward the inside of the recess.

(4) The surface material exhibits a height of rising water of 100 mm or lower, determined by the test method on water absorption of paper according to the Klemm's method, referred to in JIS P8141. This practically applies to embodiment (2).

(5) The surface material has a deformation extent at the thickness direction of 40 percent or larger at a pressure of 50 grams per square cm. This is preferably applied embodiment (2).

The invention will be explained in detail below and then each embodiment will be illustrated.

That is, according to the present invention, there is provided a surface material for sanitary articles, characterized in that said surface material comprises an opaque hydrophobic film having a top section, a bottom section and wall sections connecting said top section to said bottom section, said wall section having a slanting portion provided with an opening region in at least a portion thereof and said slanting portion provided with said opening region is not covered with said top section.

The present invention will further be described with reference to the drawings.

Figure 1:
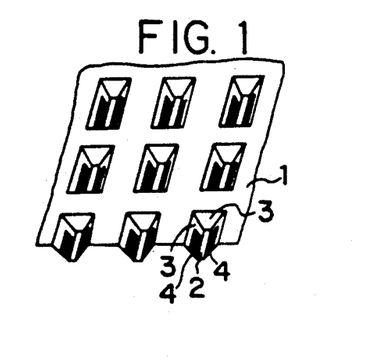
FIG. 1 is a perspective view of an example of the surface material according to the present invention.
Figure 2:
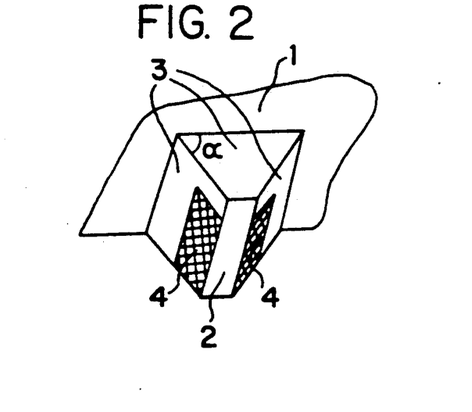
FIGS. 2 to 8 and FIGS. 10 and 11 are enlarged views of openings regions present in examples of the surface material according to the present invention.

FIG. 1 is a perspective view of a typical mode of the surface material of the present invention. FIG. 2 is an enlarged view of the opening region thereof. The surface material of the present invention comprises an opaque hydrophobic film having a top section 1, a bottom section 2 and wall sections 3 connecting them to each other. The wall section 3 has a slanting portion. At least part of the slanting portion is provided with an opening region 4. The slanting portion having an opening region is not covered with a top section 1. The opening region 4 allows for passage of a liquid excreted from a human body.

As is different from a hydrophobic film having an opening of tapering capillary form as disclosed in Japanese Patent Publication No. 17081/1982, the surface material of the present invention is highly effective in preventing the absorbed liquid from returning from the absorbent to the surface (hereinafter referred to as "liquid return preventive effect") and in covering the colored portion, formed by the absorption of a colored liquid, of the absorbent (hereinafter referred to as "covering effect") even when a large opening permitting rapid transfer of a liquid excreted from a human body (hereinafter referred to as "liquid permeability") is provided, because the wall section thereof has a slanting portion provided with an opening region. Moreover, since the slanting portion having an opening region is not covered with the top section, the openings are retained in the surface material and liquid permeability does not decrease, even when a high pressure is applied to the absorbent articles by the body of the wearer. By contrast, when the slanting portion having an opening region is covered with the top section, the openings are clogged with the top section upon application of a pressure thereto, thereby causing liquid permeability to markedly decrease. This does not meet the object of the present invention.

Another important advantage attained by providing the slanting portion of the wall section with an opening region is that a liquid is promptly removed from the body surface of the wearer and that the liquid flows at a place apart from the body surface. As a result, the skin of the wearer can be kept dry (hereinafter referred to as "surface dryness"). Thus, the absorbent articles ca be used comfortably.

The apparent thickness of the surface material, i.e., the distance between the top section and the bottom section may be arbitrarily chosen as far as a sufficient liquid return preventive effect and surface dryness are ensured. However, it is generally preferred that the thickness be 0.1 to 5 mm.

The size and density of the opening may be arbitrarily chosen as far as an appropriate balance is established among liquid permeability, liquid return preventive effect and covering effect. However, it is generally preferred that the size of the opening be 0.02 to 30 mm$^2$ and that its density be 1 to 100/cm$^2$.

The angle which the plane involving the top section connected to the wall section having an opening region makes with the slanting portion ($\alpha$ in FIG. 2) may be arbitrarily chosen as far as the opening region is not covered with the top section, that is, smaller than a right angle. However, it is generally preferred that the angle be 20° or more to ensure sufficient liquid return preventive and covering effects.

It is necessary for the hydrophobic film employed in the present invention to be opaque. Since a hydrophobic film itself is opaque, the surface material having an opening region according to the present invention is also opaque. The surface material can be suitably used as a surface material for absorbent articles absorbing a colored liquid such as menstrual blood. The opaqueness of the surface material having an opening region is numerically evaluated in terms of whiteness (see Examples). It is preferred that the whiteness be 20% or more There are various methods for providing the film with opaqueness. For example, opaqueness can be provided by adding a white pigment, such as titanium oxide or zinc oxide, to a resin in the film manufacturing step. Also, opaqueness can be provided by coating a film surface with a blend of a white pigment with an appropriate binder such as acrylic, vinyl or rubber binders. The methods for providing opaqueness are not limited, to the above-described ones so long as necessary opaqueness can be provided.

The major component of the hydrophobic film may be any arbitrary hydrophobic resin such as a polyolefin, a copolymer of an olefin with acrylic esters, vinyl acetate and other monomers, a polyester, a polyamide, cellulose acetate or the like. Generally, however, a polyolefin and a copolymer of an olefin with other monomer are preferred from the viewpoint of hand and drape.

The opening region is formed in a hydrophobic film by, e.g., meshing of protruding and recessed dies, such as embossing, by vacuum suction, or by pneumatic pressurization. An appropriate method should be chosen in accordance with the resin constituting the hydrophobic film and the type of the opening as desired.

Returning to the drawings, typical examples of the surface material of the present invention will be described.

Figure 3:
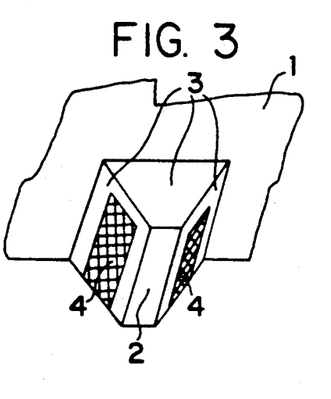

In the surface material of FIG. 2, a bottom section 2 is formed adjacent to an opening region 4. However, as shown in FIG. 3, a bottom section may be disposed apart from an opening region 4. In this connection, in the case of the surface material of FIG. 2, a liquid excreted onto the bottom section is promptly transferred to the absorber through the opening region 4. On the other hand, in the case of the surface material of FIG. 3, there is a possibility that liquid might be retained in the space defined by the bottom section 2 and the wall sections 3. Therefore, the structure as shown in FIG. 2 is preferred.

Figure 4:
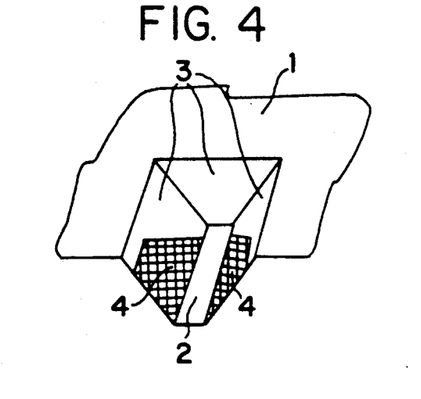
Figure 5:
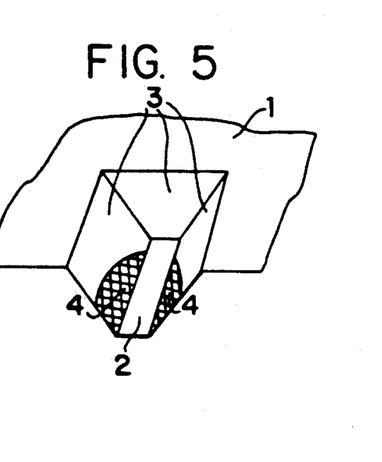
Figure 6:
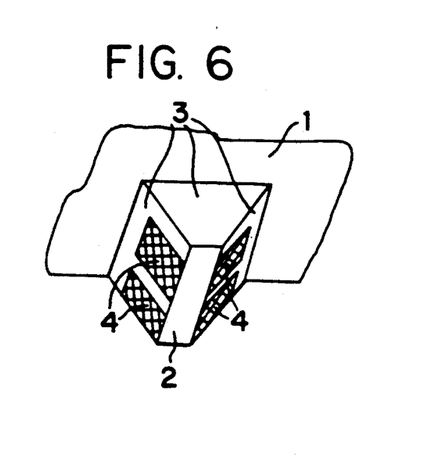
Figure 7:
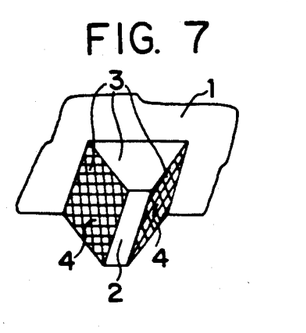

In either of FIGS. 2 and 3, the opening region 4 of the surface material is rectangular. However, its shape is not particularly limited, for it may be of arbitrary form. For example, as shown in FIGS. 4 and 5, the opening region may be trapezoidal and semicircular. Moreover, as shown in FIG. 6, a plurality of opening regions 4 may be formed on one slanting portion of a wall section. Also, as shown in FIG. 7, an opening region 4 may be formed over the entire region of one slant part of a wall section 3.

Figure 8:
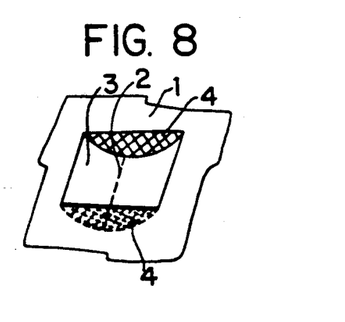
Figure 9:
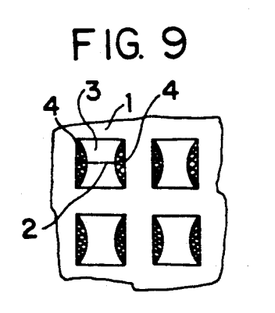
FIG. 9 is a plan view of the surface material having an opening region shown in FIG. 8.

In an example as shown in FIG. 8, a wall section 3 having no opening is of the form of a circular segment. An opening region 4 is formed over the entire region of the adjacent semicircular slanting portions of the wall section. FIG. 9 is a plan view of the same as viewed from the upside. In this case, the bottom section is represented as a point or line at which the distance from the top section plane is the maximum within the wall sections.

Figure 10:
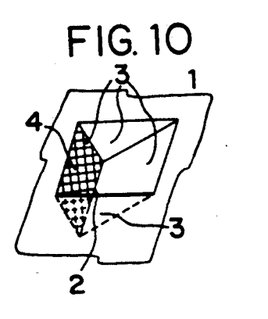

In an example shown in FIG. 10, an opening region 4 is formed in a slanting portions of a wall section surrounded by wall sections having no opening region and by a top section. A bottom section 2 is represented as line constituting a boundary between one wall section and the opening region.

Figure 11:
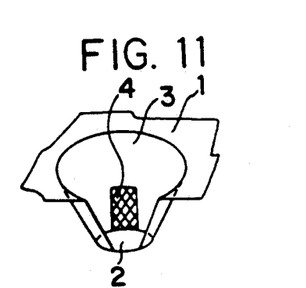

FIG. 11 shows an example in which a wall section 3 having an opening region 4 is conical. In this case as well, the number of opening regions 4, the shape thereof and whether or not a bottom section 2 is adjacent to the opening region 4 may be freely determined.

In the foregoing examples, it is not always necessary for the opening region to be present on the slanting portions of the wall section specified in the drawings. The opening may be present at any arbitrary slanting portion of the wall section, unless the opening region is covered with the top section.

As described above and as apparent from the examples of FIGS. 1 to 11, the surface material of the present invention comprises a hydrophobic opaque film having a top section, a bottom section and wall sections connecting them to each other. The wall section has a slanting portions, and at least part of the slanting portions is provided with an opening region. The slanting portions having an opening region takes a shape in which it is not covered with the top section. Consequently, even when pressure is applied thereto, fluid can freely pass the surface material. Further, fluid return is little. In the case of absorption of a colored fluid as well, coloring after absorption can be relieved. Therefore, the present surface material can be suitably employed in sanitary articles such as absorbent articles, especially a sanitary napkin for use in the absorption of a colored liquid, e.g., menstrual blood.

It is to be noted that the surface material of the present invention is not limited to the above examples and that various modifications can be made as far as the above-described requirements are met.

Embodiment (1) is explained below. In the sanitary article of the invention, the surface sheet comprises a layer consisting of a first layer made of a fibrous aggregate which is to be in contact with the skin and a second layer made of a hydrophobic porous sheet, wherein the first layer and the second layer are integrated with each other.

The second layer is prepared in the same way as shown above and details of the first layer are explained in the embodiment (2).

The liquid retention of a non-woven fabric can be improved by widening the interfiber spaces thereof and decreasing the number of the minute interfiber spaces. In the present invention, integration of a non-woven fabric layer with a porous sheet makes it possible to decrease the number of fibers of the non-woven fabric layer (namely to use a thick fiber or to decrease the basis weight thereof) to such an extent that single use of a non-woven fabric may be usually impractical because of its low strength. Therefore, the liquid retention of the non-woven fabric layer is greatly improved and the surface hand of a porous sheet can be made like that of a non-woven fabric. Further, the integration of the non-woven fabric layer with the porous sheet makes it possible to largely mitigate the above-mentioned uncomfortableness in wearing which is peculiar to the porous sheet, because the excretion rapidly reaches the porous sheet by virtue of diffusion thereof due to the capillary structure of the non-woven fabric layer.

The structures of the first layer and the second layer in the present invention will be described in detail.

It is desired that the first layer has a structure wherein it is difficult for a liquid to remain. The difficulty of a liquid remaining in the first layer depends on the distance between the fibers and the basis weight thereof Since the distance between the fibers can be chosen in a wide range if the basis weight is sufficiently small, it is desirable that the basis weight be in a range of 4 to 15 $g/m^2$. When the distance between the fibers is large, it is difficult for a liquid to remain in the first layer even if the basis weight is comparatively large. Thus, the distance between the fibers is desirably 40 $\mu$m or larger. Accordingly, it is most desirable that the basis weight be 4 to 15 $g/m^2$ and the distance between fibers be 40 $\mu$m or larger.

When the surface material according to the present invention comprises, as the fibrous aggregate constituting the first layer, one including a conjugate fiber consisting of two kinds of resin components satisfying such conditions that the melting point of a first resin component is higher by at least 100° C. than that of a second resin component and that the second resin component has a melt flow index of 10 to 50, heat sealing is possible. When such a fibrous aggregate is used, the surface material can be fixed to a material to be bonded thereto and disposed thereunder (for example, a polymer-laminated paper having a laminated portion facing the surface material) by heat sealing. In this case, an absorbent article having very good leak-proofness can be obtained.

The invention will be further explained in view of embodiment (2) which is most practical.

That is, according to the present invention, there is provided a surface material for sanitary articles, characterized in that said surface material has an integral two-layer structure comprising a film layer to be brought into contact with the skin and, integrally provided therewith, a fiber layer on the side of an absorbent, said film layer comprises an opaque hydrophobic resin having a top section, a bottom section and wall sections connecting said top section to said bottom section, at least part of said wall section is provided with an opening region and said bottom section is free from such region.

As can be understood from the foregoing description, the hand and drape of the three-dimensional side pore film can be improved by making use of a resin having low rigidity. However, this brings about a lowering in the liquid permeability. The present inventors have succeeded in improving the shape retentivity without spoiling the hand and drape through the integration of a three-dimensional side pore film with a fiber layer. This enabled the preparation of a surface material which is excellent in all of the four properties, i.e., the liquid permeability, the liquid return preventive effect, the covering effect, and the hand and drape.

Figures 15, 17, 18:
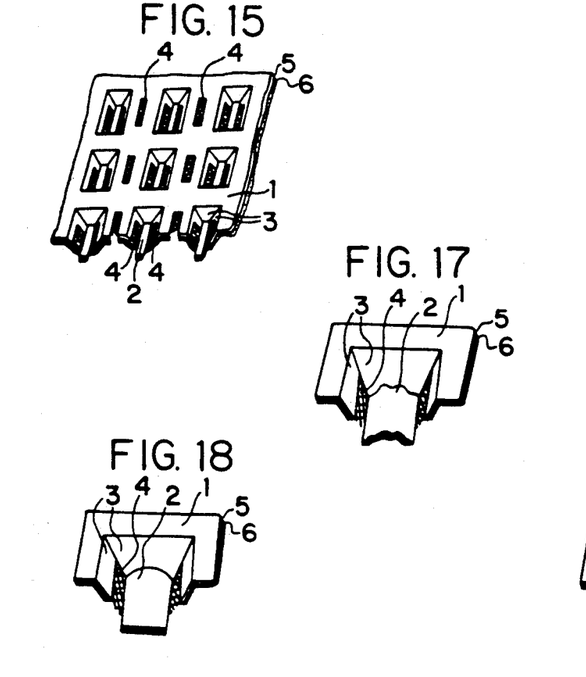
FIG. 15 shows a sheet comprising the hydrophobic film and the lined layer of fibrous aggregates.
FIGS. 16 to 19 show examples of the sheets having convex bottom portions.

The film layer and the fiber layer in the invention is described more in detail with reference to FIG. 15.

The hydrophobic film has the same FIGURE and form as shown above. In addition, opening 4 may be provided also on the land portion. See FIG. 15. It is, however, preferred from the standpoint of both liquid return preventive and covering effects that 50% or more of all the opening regions are present on the wall section 3. It is more preferable that all the opening regions be present on the wall section.

In the present invention, the opening region of the film layer can be arbitrarily provided as far as the liquid permeability, the liquid return preventive effect, and the covering effect are balanced with each other However, it is generally preferred that the size and the density of the opening be 0.1 to 2 mm$^2$ and 10 to 100/cm$^2$, respectively.

In order to impart a sufficient covering effect to the surface material, it is necessary that the film layer be opaque When the film layer is opaque, the surface material of the present invention is also opaque. This surface material can be suitably used as a surface material for absorbent articles absorbing a colored liquid such as menstrual blood. The opaqueness of the surface material is numerically expressed in terms of whiteness (see Examples). It is preferred that the whiteness be 10% or more.

There are various methods for providing the opaqueness. For example, the opaqueness can be provided by adding a white pigment to a resin in the manufacturing step of a film. Also, the opaqueness can be provided by coating a film surface with a blend of a white pigment with an appropriate binder. The methods for providing opaqueness are not limited, however, to the above-described methods as far as necessary opaqueness can be provided.

The resin for forming the film layer may be any arbitrary hydrophobic resin. Examples of the resin include a polyolefin, a copolymer of an olefin with other monomer (such as vinyl acetate or ethyl acrylate), a synthetic resin such as polyester, nylon, or acetate and a polyblend thereof. Generally, however, a polyolefin, a copolymer of an olefin with other monomer, and a polyblend thereof are preferred from the viewpoint of hand and drape and the processability in the actual production. Among them, low-density polyethylene, linear low-density polyethylene or an ethylene-vinyl acetate copolymer or a blend thereof is more preferable.

Although the thickness of the film layer may be far smaller than that of the case where a three-dimensional side pore film is used alone, it is preferably 3 to 50 $\mu$m from the viewpoint of the hand and drape and the covering effect, more preferably 10 to 40 $\mu$m.

Further, in order to regulate the liquid permeability and the liquid return preventive effect, it is possible to impart a hydrophilic nature to the surface of the film layer through a physical treatment, such as application of a surfactant and plasma radiation, or a chemical treatment, such as a treatment with a mineral acid. Furthermore it is possible to impart water repellency to the surface of the film layer through application of a silicone or fluorinated chemical.

Further, according to need, such as a need with respect to an improvement in the hand and drape, the film layer may be calendered or embossed for imparting a fine pattern thereto.

The term "fiber layer" used in the present invention is intended to mean the so-called weave comprising fibers slightly interlaced with each other and unwoven fabric or paper in which the fibers are fixed to each other by interlacing or adhesion.

The fiber may be used in any composition in the present invention. However, it is preferred from the viewpoint of the shape retentivity that synthetic fibers, such as polyolefin, polyester, acrylic, or polyamide fibers, be contained in an amount of 50% by weight or more. Among the above-described fibers, polypropylene, polyester, polyethylene/polypropylene composite fiber, polyethylene/polyester composite fiber, and composite fibers of a low melting point-having polyester and another polyester are more preferable because they have excellent elasticity and readily bring about stable hand and drape. When a synthetic fiber is used, it is preferred from the viewpoint of the liquid permeability that the surface of the fiber be subjected to a treatment for imparting a hydrophilic nature by a suitable method. In general, the thickness of the fiber is preferably 1 to 10 deniers from the viewpoint of the liquid permeability and the hand and drape.

The basis weight of the fiber layer may be arbitrarily selected as far as the surface material has sufficient shape retentivity and excellent hand and drape. However, in general, the basis weight or weight per unit area of the fiber layer is preferably 5 to 100 g/m$^2$, more preferably 10 to 50 g/m$^2$.

Representative processes for preparing the surface material of the present invention are classified broadly into the following two processes.

The first process comprises integrating a film free from an opening region with a fiber layer by means of thermal adhesion or an adhesive and perforating the resulting integral structure. This process is advantageous in productivity over the following process because it is possible to use in this process the so-called laminate film prepared by integrating a film with a fiber layer in the step of melt-extruding a starting resin to prepare a film.

The second process comprises perforating only a film free from an opening region to form a three-dimensional side pore film and integrating the film with a fiber layer The integration may be conducted through adhesion by means of thermal adhesion or an adhesive and interlacing by means of an air stream or a high-pressure water stream.

With respect to the film layer and the fiber layer, it will suffice when they are integrated with each other to such an extent that there is caused no peeling between them when the sanitary article is mounted for use. When the integration is conducted by adhesion, the adhesion sites may be uniformly distributed on the boundary surface or may be distributed in a patterned form.

It is to be noted that the surface material of the present invention is not limited to the above examples and that various modifications can be made as far as the above-described requirements are met.

Embodiment (3) having the convex bottom portion in the recesses is described below with reference to FIGS. 16 to 21.

The surface sheet of embodiment (3) comprises a hydrophobic film having a top section, a substantially upward protruding bottom section and wall sections connecting said top section to said bottom section, at least part of said wall section is provided with an opening region and said bottom section is free from such region.

Figure 16:
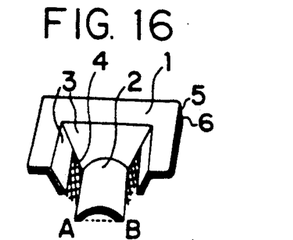

The present inventors have succeeded in remarkably improving the permeability to a highly viscous liquid through a remarkable decrease in the amount of the highly viscous liquid retained on the bottom section 2 by forming the bottom section 2 of the three-dimensional side pore sheet into substantially upward protruding configuration as shown in FIG. 16. This enabled the preparation of a surface material having sufficient permeability to a highly viscous liquid and excellent liquid return preventive and covering effects.

The surface material of the present invention consists of only a hydrophobic film layer having the above-described configuration or consists of a hydrophobic film layer having the above-described configuration and to be brought into contact with the skin and a fiber layer provided on the side of an absorbent integrally with said hydrophobic film layer.

Figure 19:
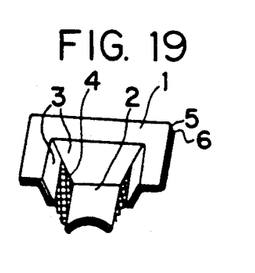
Figure 20:
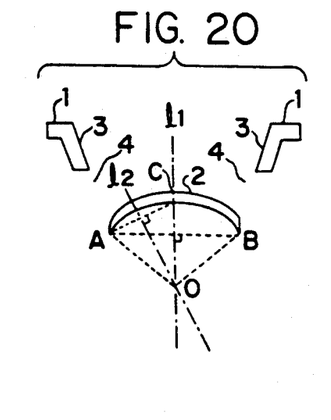
FIG. 20 explains the definition of the convex form on the bottom portion.

The term "upward protruding" used in the present invention is intended to mean that among the cross sections crossing at least one opening region 4 there is one satisfying a requirement that a line AB connecting both ends of the bottom section 2 adjacent to the wall section 3 having the opening region 4 must be located below the bottom section 2, i.e., on the side of the absorbent as shown in FIG. 20. The degree of the "upward protrusion" is numerically expressed in terms of the radius of curvature (see Examples). In order to attain a sufficient liquid permeability to a highly viscous liquid, the radius of curvature is preferably 2.5 mm or less, more preferably 1.5 mm or less. However, the cross section of the bottom section is not necessarily arcuated strictly but may have fine undulations as long as the bottom section is substantially arcuated as a whole as shown in FIG. 17. Further, the entire bottom section is not necessarily upward protruding as long as the bottom section is partially upward protruding. For example, as shown in FIG. 18, when the end part of the bottom section 2 or its vicinity is upward protruding, the central part or its vicinity may be flat. On the contrary, as shown in FIG. 19, when the central part of the bottom section 2 or its vicinity is upward protruding, the end part or its vicinity may be flat. That is, in order to rapidly absorb a highly viscous liquid, the entire bottom section is not necessarily upward protruding. However, it is desired that 60% or more, preferably 70% or more, of the bottom section be upward protruding.

Embodiment (4) is characterized in that satisfactory liquid return preventive and covering effects can be attained without substantially lowering the liquid permeability by decreasing the diffusion and retention of the liquid in the fiber layer through the use of a hydrophobic fiber or a hydrophilic fiber which has been subjected to a sufficient treatment for imparting a hydrophobic nature, which has led to the completion of the present invention.

In the invention, the surface sheet has an integral two-layer structure comprising a film layer to be brought into contact with the skin and having an opening region provided in at least part thereof and, integrally provided therewith, a fiber layer on the side of an absorber and said surface material having an integral structure exhibits a height of the rise of water of 100 mm or less as determined by the testing method of water absorption of paper by Klemm's method (JIS-P8141).

With respect to the fiber layer, in order to provide satisfactory liquid return preventive and covering effects, it is necessary to regulate the water absorptivity so that the fiber layer in a state of an integration with the surface material, i.e., the film layer, exhibits a height of the rise of water of 100 mm or less as determined by the testing method of water absorption of paper by Klemm's method (JIS-P8141) (hereinafter referred to as the "Klemm water absorption").

The fiber layer may comprise a web composed of fibers slightly interlaced with each other, a nonwoven fabric or paper in which the fibers are fixed to each other by interlacing or adhesion. However, it is preferred from the viewpoint of the liquid permeability and the liquid return preventive effect that the fiber layer comprise a nonwoven fabric or paper. With consideration given to the hand and drape as well, a nonwoven fabric is more preferable, and a dry heat-bonded nonwoven fabric is further preferable. Since the fibers are not fixed to each other in the web, the fiber layer is easily broken when the use moves. This may bring about a lowering in the liquid permeability and the liquid return preventive effect. In the paper, there is a limitation with respect to an improvement in the hand and drape. On the other hand, in the nonwoven fabric, particularly dry heat-bonded nonwoven fabric, since not only the fibers are firmly fixed to each other but also the nonwoven fabric exhibits excellent flexibility, it is possible to prepare a surface material which is excellent in liquid permeability, liquid return preventive effect, and hand and drape.

Further, the fiber layer may have a structure wherein the composition is discontinuously varied in the thicknesswise direction thereof In this case, it is more preferred from the viewpoint of an improvement in both liquid return preventive and covering effects that the fibers be arranged so that the hydrophilic nature is enhanced with an increase in the distance from the film layer.

Various fibers may be used as the fiber for constituting the fiber layer. Examples of the fiber include hydrophilic fibers, such as wooden pulp, rayon and vinylon, which have been subjected to a treatment for imparting a hydrophobic nature according to a known method and hydrophobic fibers such as polyolefin, polyester, acrylic and polyamide fibers. However, it is preferred from the viewpoint of the liquid return preventive effect and the hand and drape that the fiber layer be composed mainly of a hydrophobic fiber. Further, as mentioned above, it is preferred that the fiber layer be a dry heat-bonded nonwoven fabric When this matter is taken into account, preferable fibers among the above-described hydrophobic fibers are heat-bondable fibers, such as polyethylene/polypropylene composite fiber, composite fibers of polyethylene and a polyester and composite fibers of a low melting point-having polyester and another polyester. Further, with consideration given to the adhesion to the film layer, preferable fibers among the above-described composite fibers are polyethylene/polypropylene composite fiber and polyethylene/polyester composite fiber. In the use of the hydrophobic fiber, when a further improvement in the liquid permeability and the liquid return preventive effect is required, it is possible to conduct a treatment for imparting a suitable hydrophilic nature or water repellency. Further, when a further improvement in both liquid return preventive and covering effects is required, modified cross section fibers thereof, such as a multifoliate cross section, may be used.

In general, the fineness of the fiber is preferably 1 to 10 deniers, more preferably 1.5 to 6 deniers.

The basis weight of the fiber layer is preferably 5 to 100 g/m², more preferably 10 to 50 g/m² from the viewpoint of the liquid return preventive effect and the hand and drape.

It is preferred from the viewpoint of the liquid permeability that the fiber density of the fiber layer in the opening of the film layer be lower than that of the fiber layer in the region of the film layer free from any opening. It is more preferred that the fiber be absent in an area of 10% or more based on the area of the opening region of the film layer.

It is preferred from the viewpoint of the liquid permeability and the liquid return preventive effect that the film layer and the fiber layer be integrated with each other as firmly as possible In general, it is preferred that the peeling strength of the both layers be 50 g or more. When the integration is conducted by adhesion, the adhesion sites may be uniformly distributed on the boundary surface or may be distributed in a patterned form.

The surface material can be prepared by the processes mentioned before.

When remarkably high liquid permeability is required, it is possible to fix a sheet material, such as nonwoven fabric or web, comprising a hydrophilic fiber, such as pulp or rayon, to the rear side of the surface material by means of heat bonding or an adhesive. Further, in the above-described first process, the hydrophilic fiber sheet may be laid on the surface material, followed by perforation to integrate the sheet with the surface material.

Figure 22:
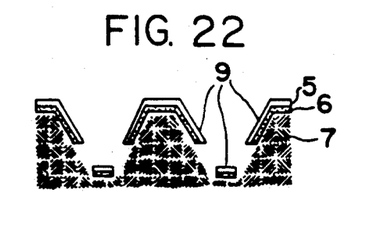
FIGS. 22 and 23 each show a combination of the sheet of surface material and an absorbent. In the drawing, the numerical reference to 1 shows the top section and the land portion; 2, the bottom portion; 3, the wall portion; 4, the opening; 5, the hydrophobic film; 6, the layer of fibrous aggregates; 7, the absorbent; 8, a sheet of fibrous absorbent; and 9, the sheet of surface material.
Figure 23:
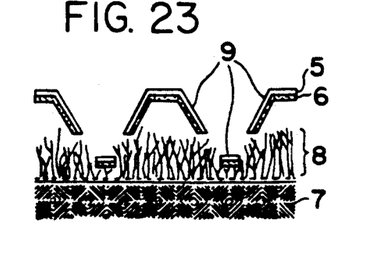

As shown in FIG. 22, a fiber layer 6 of a surface material 9 may be integrated with an absorber-constituting element 7 comprising rayon cotton, polyester cotton, pulp, or the like through interlacing by taking advantage of a differential pressure of a fluid, such as air pressure or water stream, or by means of heat bonding or a binder. Further, as shown in FIG. 23, an absorber-constituting element 7 may be covered with an absorbent fiber sheet 8 having fuzz on the surface thereof, followed by lamination thereof on a surface material 9. The above-described expedients enable a further improvement in the liquid permeability without spoiling the excellent liquid return preventive and covering effects.

Embodiment (5) is a sanitary article of the invention in which the surface sheet is formed so that 40 percent or larger of stress or deformation extent may appear at the thickness direction when it is loaded with a pressure of 50 grams per square cm. The loaded pressure corresponds to a usual pressure of compression which applies to a sanitary napkin on use. The embodiment is improved in a fit to a user who is especially doing physical exercise. Deformation of 50 percent or larger is more preferable.

Deformation extent by compression is determined in terms of an amount of deformation in view of a weight of load.

EXAMPLES

The advantages of the present invention will now be described with reference to the following Examples which should not be construed as limiting the scope of the present invention.

EXAMPLES 1 TO 23 AND COMPARATIVE EXAMPLES 1 TO 3

Surface materials having various shapes according to the present invention, together with comparative surface materials, were prepared from the resins shown in Table 1. Their properties were evaluated according to the following methods.

The results are shown in Table 1.

All of the surface materials were prepared by providing the resin in the film form with an opening region by embossing. All of the surface materials, except that of Comparative Example 1, contained titanium oxide as a white pigment in an amount of about 10% by weight.

To evaluate the absorption time, liquid return and visual dryness, a model napkin was prepared by removing a surface material from a commercially available sanitary article, i.e., Laurier (a product of Kao Corp.) and then attaching each surface material thereto.

Measuring method (1) Size of opening:

A magnified photograph of an opening region as viewed from a direction perpendicular thereto was taken with a stereomicroscope to measure the size, a, of each opening on the photograph with a planimeter. From the value of a, the real size, A, of the opening was calculated according to the following equation (1):

$$A \text{ (mm}^2\text{)} = \frac{a \text{ (mm}^2\text{)}}{X^2} \quad (1)$$

wherein X represents the magnification of the photograph of the original.

(2) Density of opening:

The density was determined by counting the number of openings per cm² of a surface material.

Figure 14:
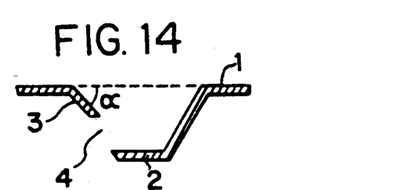
FIGS. 14 and 21 each explain how to determine an angle of the opening.

(3) Opening angle:

The cross section of a surface material was photographed as shown in FIG. 14 with a stereomicroscope to measure the angle, α, with a protractor. The measured angle was defined as the "opening angle".

(4) Degree of whiteness:

Under the same illumination conditions, the absolute reflectance, $R_0$, of the standard red-color mount with respect to a light of 500 nm (green) in wavelength and the absolute reflectance, R, of each surface material sample with respect to the light of the same wavelength were measured with a model ND-101 DP colorimetrical color difference meter manufactured by Nippon Denshoku Kogyo Co., Ltd., and the degree of whiteness, $R_r$, of each surface material sample was calculated according to the following equation (2). The operation was conducted in accordance with the "Instruction Manual for ND-101DP".

$$R_r (\%) = \frac{R - R_0}{100 - R_0} \times 100 \quad (2)$$

(5) Absorption time and amount of returned liquid:

10 ml of a test solution was injected at a pressure of 5 g/cm², and the time taken for the solution to be absorbed into the model napkin was measured. The measured time was defined as the "absorption time", and a smaller value of this time means a greater liquid permeability. Further, after a predetermined period of time, a pressure of 50 g/cm² was applied and the amount of the test solution which had returned from the inside through the surface material was determined. The determined amount was defined as the "amount of returned liquid", and a smaller value of this amount means a smaller surface stickiness and a more comfortableness at the time of use.

(6) Visual dryness:
The following ranking was made by an organoleptic test on the state of the model napkin after absorption of 4 g of an equine defibrinated blood:

⊙: red color derived from blood is not observed at all.
○: red color derived from blood is slightly observed.
Δ: red color derived from blood is significantly observed.
X: red color derived from blood is very clearly observed.

As is apparent from Examples 1 to 23, the surface material of the present invention is small in the absorption time and the amount of returned liquid and excellent in the visual dryness, which renders the surface material of the present invention suitable for use in absorbent articles, especially a sanitary napkin for use in the absorption of a colored liquid such as menstrual blood.

In Comparative Example 1, since the whiteness of the film itself was low, the color of the test solution which had diffused into the absorber was observable through the film. Therefore, the visual dryness was poor.

In Comparative Example 2, an opening region was formed at the bottom section of the surface material, which lowered the whiteness of the surface material, thereby given a poor visual dryness. Moreover, the amount of returned liquid was large, and hence it cannot be stated that the surface material has properties requisite for a surface material used in absorbent articles.

In Comparative Example 3, since the opening angle was greater than 90°, the opening region was clogged when a pressure was applied, resulting in an extremely long absorption time. Therefore, it is apparent that the surface material is quite unsuitable as a surface material for use in absorbent articles.

TABLE 1

Figure 12:
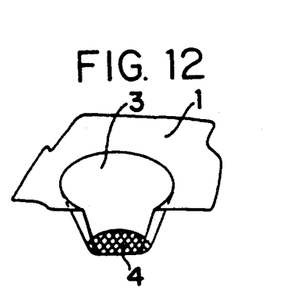
FIGS. 12 and 13 are enlarged views of opening regions present in comparative surface materials.
Figure 13:
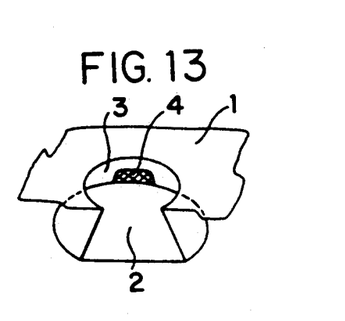

| | film-constituting resin | shape | size of opening (mm$^2$) | density of opening (per cm$^2$) | opening angle (°) | degree of whiteness (%) | absorption time (sec) | amount of returned liquid (g) | visual dryness |
|---|---|---|---|---|---|---|---|---|---|
| Ex. | | | | | | | | | |
| 1 | LDPE[1] | FIG. 2 | 0.05 | 31 | 61 | 75 | 49 | 0.01 | ⊙ |
| 2 | " | " | 0.11 | 31 | 60 | 62 | 38 | 0.02 | ⊙ |
| 3 | " | " | 5.03 | 29 | 60 | 48 | 21 | 0.05 | ○ |
| 4 | " | " | 0.04 | 4 | 60 | 85 | 61 | 0.01 | ⊙ |
| 5 | " | " | 0.12 | 5 | 62 | 77 | 59 | 0.01 | ⊙ |
| 6 | " | " | 4.95 | 5 | 62 | 47 | 43 | 0.04 | ⊙ |
| 7 | " | " | 0.05 | 91 | 58 | 52 | 27 | 0.03 | ⊙ |
| 8 | " | " | 0.10 | 93 | 59 | 43 | 20 | 0.06 | ○ |
| 9 | " | " | 5.01 | 88 | 61 | 36 | 10 | 0.11 | ○ |
| 10 | " | " | 0.05 | 30 | 29 | 63 | 39 | 0.02 | ○ |
| 11 | " | " | 0.09 | 30 | 31 | 51 | 24 | 0.04 | ○ |
| 12 | " | " | 5.00 | 31 | 32 | 44 | 18 | 0.10 | ○ |
| 13 | " | " | 0.05 | 32 | 80 | 79 | 56 | 0.01 | ⊙ |
| 14 | " | " | 0.11 | 30 | 82 | 68 | 37 | 0.01 | ⊙ |
| 15 | " | " | 4.98 | 31 | 81 | 61 | 25 | 0.02 | ⊙ |
| 16 | EVA[2] | " | 0.10 | 29 | 60 | 61 | 30 | 0.02 | ⊙ |
| 17 | EEA[3] | " | 0.11 | 31 | 60 | 62 | 32 | 0.02 | ⊙ |
| 18 | ionomer[4] | " | 0.11 | 30 | 59 | 60 | 31 | 0.02 | ⊙ |
| 19 | LDPE | FIG. 3 | 0.12 | 38 | 60 | 61 | 49 | 0.04 | ○ |
| 20 | " | FIG. 7 | 0.25 | 29 | 61 | 47 | 20 | 0.06 | ○ |
| 21 | " | FIG. 8 | 0.12 | 31 | 60 | 63 | 28 | 0.03 | ⊙ |
| 22 | " | FIG. 10 | 0.15 | 28 | 62 | 58 | 27 | 0.03 | ⊙ |
| 23 | " | FIG. 12 | 0.10 | 30 | 63 | 61 | 35 | 0.02 | ⊙ |
| Comp. Ex. | | | | | | | | | |
| 1 | LDPE | FIG. 2 | 0.09 | 30 | 62 | 7 | 37 | 0.02 | X |
| 2 | " | FIG. 12 | 0.10 | 29 | 0 | 18 | 22 | 2.01 | Δ |
| 3 | " | FIG. 13 | 0.11 | 30 | 118 | 88 | 683 | 0.01 | ⊙ |

Note:
[1]Low-density polyethylene
[2]Ethylene-vinyl acetate copolymer
[3]Ethylene-ethyl acrylate copolymer
[4]Ionic crosslinked ethylene-acrylic acid copolymer The embodiment (2) of the invention is worked below.

EXAMPLES 1 TO 45 AND COMPARATIVE EXAMPLES 1 to 5

Various surface materials shown in Tables 4 to 7 were prepared by making use of a film layer shown in Tables 1 and 2 and a fiber layer shown in Table 3 as the constituent materials.

The methods of determining the physical properties of each constituent materials and each surface material will now be described. Values of the physical properties are each an average of 10 measured values.

Figure 21:
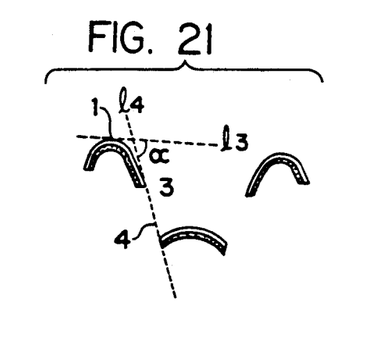

The cross section of a surface material was photographed as shown in FIG. 14 to measure the angle represented by a letter α with a protractor. The measured angle was defined as the "slant angle". Further, the thickness, t, of the surface material on the photograph was measured with a ruler to calculate the real thickness, T, of the surface material according to the following equation (2). When the surface material is curved as shown in FIG. 21, an angle of intersection of a tangent $l_1$ on the upper end of the top section and a straight line $l_2$ passing through both ends of the opening region was defined as the slant angle, α.

$$T \, (\mu m) = 1,000 \, t \, (mm)/x \ldots \quad (2)$$

wherein x represents the magnification of the photograph of the original.

To evaluate the physical properties of each surface material, a model napkin was prepared by removing a surface material from a commercially available sanitary article, i.e., Laurier (a product of Kao Corp.), and then attaching each surface material thereto.

①  Absorption time and amount of returned liquid 10 g of an equine defibrinated blood was injected into the model napkin at a pressure of 5 g/cm$^2$, and the time taken for the blood to be absorbed into the model napkin was measured. The measured time was defined as the "absorption time". In general, a smaller value of this time means a greater liquid permeability After a predetermined period of time, the pressure was increased to 50 g/cm$^2$, and the amount of the test solution which had returned from the inside through the surface material was determined. The determined amount was defined as the "amount of returned liquid", and a smaller value of this amount means a smaller surface stickiness and a more comfortableness at the time of use.

② Hand and drape

The following ranking was made with respect to the touch of the model napkin:

3rd grade: the touch is very soft.

2nd grade: the touch is soft.

1st grade: the touch is so hard that it is unsuitable for use as a surface material.

③ Visual dryness

The following ranking was made with respect to the state of the model napkin after abroption of 4 g of an equine defibrinated blood:

4th grade: red color derived from blood is not observed at all.

3rd grade: red color derived from blood is slightly observed.

2nd grade: red color derived from blood is significantly observed.

1st grade: red color derived from blood is very clearly observed to such an extent that the red color gives unpleasantness.

TABLE 1

| | | | film layer (1) | | | | | | |
|---|---|---|---|---|---|---|---|---|---|
| No. | resin | size of opening (mm$^2$) | density of opening (per cm$^2$) | slant angle (°) | thickness (μm) | TiO$_2$ content (%) | degree of whiteness (%) | distribution of openings | surface treatment |
| I-1 | LLDPE | 0.02 | 48 | 59 | 10 | 15 | 62 | A-1 | B-1 |
| I-2 | " | 0.21 | 50 | 60 | 10 | 15 | 41 | " | " |
| I-3 | " | 5.03 | 50 | 58 | 12 | 15 | 32 | " | " |
| I-4 | " | 0.09 | 5 | 57 | 9 | 15 | 51 | " | " |
| I-5 | " | 0.22 | 138 | 60 | 12 | 15 | 28 | " | " |
| I-6 | " | 0.21 | 51 | 31 | 11 | 15 | 32 | " | " |
| I-7 | " | 0.21 | 50 | 77 | 11 | 15 | 59 | " | " |
| I-8 | " | 0.19 | 52 | 101 | 10 | 15 | 85 | " | " |
| I-9 | " | 0.20 | 49 | 144 | 10 | 15 | 92 | " | " |
| I-10 | " | 0.20 | 48 | 60 | 6 | 14 | 33 | " | " |
| I-11 | " | 0.21 | 51 | 59 | 34 | 15 | 55 | " | " |
| I-12 | " | 0.20 | 49 | 58 | 97 | 15 | 62 | " | " |

Note:
LLDPE: linear low-density polyethylene (a product of Mitsui Petrochemical Industries, Ltd.)
A-1: all the openings are present in the wall section.
B-1: untreated

TABLE 2

| | | | film layer (2) | | | | | | |
|---|---|---|---|---|---|---|---|---|---|
| No. | resin | size of opening (mm$^2$) | density of opening (per cm$^2$) | slant angle (°) | thickness (μm) | TiO$_2$ content (%) | degree of whiteness (%) | distribution of openings | surface treatment |
| I-13 | LLDPE | 0.22 | 48 | 61 | 10 | 15 | 34 | A-2 | B-1 |
| I-14 | " | 0.20 | 51 | 59 | 9 | 15 | 28 | A-3 | " |
| I-15 | " | 0.22 | 50 | 58 | 12 | 15 | 12 | A-4 | " |
| I-16 | " | 0.20 | 49 | 61 | 12 | 15 | 40 | A-1 | B-2 |
| I-17 | " | 0.20 | 48 | 59 | 9 | 15 | 39 | " | B-3 |
| I-18 | " | 0.20 | 50 | 60 | 11 | 15 | 42 | " | B-4 |
| I-19 | " | 0.21 | 52 | 62 | 11 | 20 | 52 | " | B-1 |
| I-20 | " | 0.18 | 51 | 58 | 12 | 10 | 29 | " | " |
| I-21 | " | 0.19 | 49 | 61 | 10 | 0 | 5 | " | " |
| I-22 | LDPE | 0.18 | 50 | 60 | 12 | 14 | 39 | " | " |
| I-23 | EVA | 0.20 | 50 | 59 | 11 | 14 | 38 | " | " |
| I-24 | Tafmer | 0.21 | 47 | 58 | 12 | 16 | 41 | " | " |
| I-25 | blend | 0.20 | 49 | 62 | 9 | 15 | 40 | " | " |

Note:
LDPE: low-density polyethylene (a product of Mitsui Petrochemical Industries, Ltd.)
EVA: ethylene-vinyl acetate copolymer (a product of Mitsui Petrochemical Industries, Ltd.)
Tafmer: ethylene-α-olefin copolymer (a product of Mitsui Petrochemical Industries, Ltd.)
blend: LLDPE-LDPE-Tafmer blend
A-2: the openings are present in the following ratio: the wall section/the top section = 70/30.
A-3: the openings are present in the following ratio: the wall section/the top section = 30/70.
A-4: all the openings are present in the bottom section.
B-2: a treatment for imparting a hydrophilic nature was conducted by application of a surfactant (Pelex; a product of Kao Corp.)
B-3: a treatment for imparting a hydrophilic nature was conducted by plasma radiation in an argon gas atmosphere.
B-4: a treatment for imparting a hydrophobic nature was conducted by application of a fluorinated repellent (Bosui; a product of Sony Chemical Corp.)

TABLE 3

| kind | | composition 1st layer | | | composition 2nd layer | | | basis weight (g/m²) | treatment of surface for imparting hydrophilic nature |
|---|---|---|---|---|---|---|---|---|---|
| II-1 | heat-bonded nonwoven fabric | ES SH | 2d 2d | 40% 60% | ES PET | 2d 6d | 35% 65% | 11 | yes |
| II-2 | heat-bonded nonwoven fabric | ES SH | 2d 2d | 40% 60% | ES PET | 2d 6d | 35% 65% | 20 | |
| II-3 | heat-bonded nonwoven fabric | ES SH | 2d 2d | 40% 60% | ES PET | 2d 6d | 35% 65% | 38 | |
| II-4 | heat-bonded nonwoven fabric | SH | 3d | 100% | SH PET | 3d 6d | 35% 65% | 20 | |
| II-5 | heat-bonded nonwoven fabric | SH | 3d | 100% | SH Ray | 3d 3d | 20% 80% | 20 | |
| II-6 | heat-bonded nonwoven fabric | ES PET | 1.5d 2d | 60% 40% | | | | 15 | |
| II-7 | high-pressure fluid-interlaced nonwoven fabric | ES Ray | 1.5d 3d | 50% 50% | | | | 30 | |
| II-8 | spun-bonded nonwoven fabric | | polyester | | | | | 20 | |
| II-9 | spun-bonded nonwoven fabric | | rayon | | | | | 28 | no |
| II-10 | dry-binder nonwoven fabric | | rayon | | | | | 40 | |
| II-11 | wet nonwoven fabric | | rayon | | | | | 30 | |
| II-12 | water-absorptive paper | | kraft pulp | | | | | 33 | |
| II-13 | web | | kraft pulp | | | | | 21 | |
| II-14 | web | Ray | 3d | 100% | | | | 15 | |
| II-15 | web | PET | 2d | 100% | | | | 20 | yes |

Note:
II-1 to II-6: a predetermined fiber was formed into a web with a miniature card, followed by hot-air treatment.
II-7: a predetermined fiber was formed into a web with a miniature card, followed by high-pressure water stream treatment.
II-8: "Aiel"; a product of Asahi Chemical Industry Co., Ltd.
II-9: "Taiko TCF"; a product of Futamura Chemical Industries Co., Ltd.
II-10: "Counter Cloth"; a product of Kuraflex.
II-11: "Vx"; a product of Inogami Co., Ltd.
II-12: a product of Inogami Co., Ltd.
II-13: a pulp was formed into a web by the air-lay method.
II-14 and II-15: a predetermined fiber was formed into a web with a miniature card.
ES: polyethylene/polypropylene composite fiber (a product of Daiwabo Co., Ltd.)
SH: polyethylene/polyester composite fiber (a product of Daiwabo Co., Ltd.)
PET: polyester fiber (a product of Teijin Limited)
Ray: rayon fiber (a product of Daiwabo Co., Ltd.)
treatment of surface for imparting hydrophilic nature: the treatment was conducted by applying 5% by weight of Pelex OPT (a product of Kao Corp.) to the fiber layer.

TABLE 4 constitution and performance of surface material (1)

| | constitution film layer | constitution fiber layer | integration method | performance absorption time (sec) | amount of returned liquid (mg) | hand and drape (grade) | visual dryness (grade) |
|---|---|---|---|---|---|---|---|
| Ex. 1 | I-1 | II-2 | C-1 | 32 | 0.01 | 3 | 4 |
| Ex. 2 | I-2 | '' | '' | 22 | 0.02 | 3 | 4 |
| Ex. 3 | I-3 | '' | '' | 12 | 0.04 | 3 | 3 |
| Ex. 4 | I-4 | '' | '' | 43 | 0.01 | 3 | 4 |
| Ex. 5 | I-5 | '' | '' | 10 | 0.06 | 3 | 3 |
| Ex. 6 | I-6 | '' | '' | 18 | 0.05 | 3 | 3 |
| Ex. 7 | I-7 | '' | '' | 28 | 0.01 | 3 | 4 |
| Ex. 8 | I-8 | '' | '' | 55 | 0.01 | 3 | 4 |
| Ex. 9 | I-9 | '' | '' | 86 | 0.01 | 3 | 4 |
| Ex. 10 | I-10 | '' | '' | 45 | 0.03 | 3 | 3 |
| Ex. 11 | I-11 | '' | '' | 14 | 0.02 | 2 | 4 |

Note:
C-1: a resin film was laminated on a fiber layer, followed by formation of an opening region having a shape shown in FIG. 2 with an embossing roller.

TABLE 5 constitution and performance of surface material (2)

| | constitution | | | performance | | | |
|---|---|---|---|---|---|---|---|
| | film layer | fiber layer | integration method | absorption time (sec) | amount of returned liquid (mg) | hand and drape (grade) | visual dryness (grade) |
| Ex. 12 | I-13 | II-2 | C-1 | 30 | 0.03 | 3 | 3 |
| Ex. 13 | I-14 | " | " | 26 | 0.08 | 3 | 2 |
| Ex. 14 | I-16 | " | " | 7 | 0.04 | 3 | 4 |
| Ex. 15 | I-17 | " | " | 13 | 0.03 | 3 | 4 |
| Ex. 16 | I-18 | " | " | 28 | 0.01 | 3 | 4 |
| Ex. 17 | I-19 | " | " | 23 | 0.02 | 3 | 4 |
| Ex. 18 | I-20 | " | " | 21 | 0.02 | 3 | 3 |
| Ex. 19 | I-22 | " | " | 23 | 0.03 | 3 | 4 |
| Ex. 20 | I-23 | " | " | 25 | 0.03 | 3 | 4 |
| Ex. 21 | I-24 | " | " | 22 | 0.01 | 3 | 4 |
| Ex. 22 | I-25 | " | " | 24 | 0.01 | 3 | 4 |

TABLE 6 constitution and performance of surface material (3)

| | constitution | | | performance | | | |
|---|---|---|---|---|---|---|---|
| | film layer | fiber layer | integration method | absorption time (sec) | amount of returned liquid (mg) | hand and drape (grade) | visual dryness (grade) |
| Ex. 23 | I-2 | II-1 | C-1 | 28 | 0.03 | 3 | 4 |
| Ex. 24 | " | II-3 | " | 16 | 0.01 | 3 | 4 |
| Ex. 25 | " | II-4 | " | 17 | 0.01 | 3 | 4 |
| Ex. 26 | " | II-5 | " | 13 | 0.04 | 3 | 4 |
| Ex. 27 | " | II-6 | " | 19 | 0.03 | 3 | 4 |
| Ex. 28 | " | II-7 | " | 13 | 0.05 | 3 | 4 |
| Ex. 29 | " | II-8 | " | 28 | 0.03 | 3 | 4 |
| Ex. 30 | " | II-9 | " | 18 | 0.08 | 3 | 3 |
| Ex. 31 | " | II-10 | " | 23 | 0.07 | 2 | 3 |
| Ex. 32 | " | II-11 | " | 15 | 0.09 | 2 | 3 |
| Ex. 33 | " | II-12 | " | 11 | 0.15 | 2 | 3 |

TABLE 7 constitution and performance of surface material (4)

| | constitution | | | performance | | | |
|---|---|---|---|---|---|---|---|
| | film layer | fiber layer | integration method | absorbtion time (sec) | amount of returned liquid (mg) | hand and drape (grade) | visual dryness (grade) |
| Ex. 34 | I-2 | II-13 | C-2 | 13 | 0.38 | 3 | 2 |
| Ex. 35 | " | II-14 | " | 17 | 0.24 | 3 | 2 |
| Ex. 36 | " | II-15 | " | 26 | 0.21 | 3 | 3 |
| Ex. 37 | " | II-13 | C-3 | 15 | 0.35 | 2 | 2 |
| Ex. 38 | " | II-14 | " | 18 | 0.22 | 2 | 2 |
| Ex. 39 | " | II-15 | " | 35 | 0.18 | 3 | 3 |
| Ex. 40 | " | II-13 | C-4 | 14 | 0.35 | 3 | 2 |
| Ex. 41 | " | II-14 | " | 17 | 0.22 | 3 | 2 |
| Ex. 42 | " | II-15 | " | 23 | 0.24 | 3 | 3 |
| Ex. 43 | " | II-13 | C-5 | 10 | 0.42 | 2 | 2 |
| Ex. 44 | " | II-14 | " | 14 | 0.36 | 2 | 2 |
| Ex. 45 | " | II-15 | " | 20 | 0.25 | 3 | 3 |
| Comp. Ex. 4 | I-15 | II-15 | C-1 | 16 | 1.86 | 3 | 1 |
| Comp. Ex. 5 | I-21 | II-15 | C-1 | 23 | 0.02 | 3 | 1 |

Note:
C-2: a film layer alone was treated with an embossing roller to form an opening region having a shape shown in FIG. 2, followed by fixation of a fiber layer thereon by means of heat bonding.
C-3: a film layer alone was treated with an embossing roller to form an opening region having a shape shown in FIG. 2, followed by fixation of a fiber layer thereon by means of an adhesive.
C-4: a film layer alone was treated with an embossing roller to form an opening region having a shape shown in FIG. 2, followed by fixation of a fiber layer thereon by means of air pressure.
C-5: a film layer alone was treated with an embossing roller to form an opening region having a shape shown in FIG. 2, followed by fixation of a fiber layer thereon by means of high-pressure water stream.

As can be seen from Examples 1 to 45, the surface material of the present invention is small in the liquid absorption time and the amount of returned liquid and excellent in the visual dryness as well as in the hand and drape. Particularly, the samples of Examples of 1, 2, 6, 7, 10 to 12, and 14 to 33 are found to be improved in respect to the liquid return preventive effect and visual dryness and therefore are ideal surface materials.

In Comparative Example 4, since all the openings were present in the bottom section, the liquid return preventive effect and the visual dryness were poor. Further, in Comparative Example 5, since the film layer was free from a white pigment, the degree of whiteness was low This caused the color of the liquid which had diffused into the nonwoven fabric layer or the absorber to be in sight through the surface material Therefore, the visual dryness was poor.

The embodiment (3) of the invention is worked below.

EXAMPLES 1 TO 11

Various surface materials shown in Table 3 were prepared by making use of a film layer shown in Table 2 and a fiber layer shown in Table 1 as the components. Titanium oxide was added as a white pigment in an amount of 15% to each film layer.

In all Examples except for Example 11, a film was integrated through thermal adhesion with a fiber layer comprising a nonwoven fabric prepared by dry thermal adhesion having a composition shown in Table 1 in the step of melt extruding a starting resin to prepare a film layer, and the resulting integral structure was perforated with an embossing roller to form a predetermined opening region.

In Example 11, a film layer alone was perforated with an embossing roller to form a predetermined opening region.

Physical properties are determined on the average of 10 samples and in the same way as shown before, except for the following.

A photograph of a cross section of a surface material was taken as shown in FIG. 20. The point of intersection of a perpendicular bisector $l_1$ of a line AB connecting both end parts of the bottom section 4 to each other and the bottom section 4 was designated as C. On the other hand, the point of intersection of a perpendicular bisector $l_2$ of a line AC and $l_2$ was designated as O. Then, the length of the line AO, r (mm), was determined, to calculate the radius of curvature, R (mm), according to the following equation (1):

$$R = r/x \ldots \quad (1)$$

wherein x represents the magnification of the photograph of the original.

Highly viscous liquid absorption time and amount of returned liquid:

10 g of an aqueous 1% carboxymethylcellulose solution was injected into the model napkin under a predetermined pressure, and the time taken for the solution to be absorbed into the assumed sample was measured. The measured time was defined as the "absorption time", and a smaller value of this time means a greater liquid permeability. Then, the pressure was increased, and the amount of the test solution which had returned from the inside through the surface material was measured The determined amount was defined as the "amount of returned liquid", and a smaller value of this amount means a smaller surface stickiness and a more comfortableness at the time of use.

TABLE 1

| composition | fiber layer | |
|---|---|---|
| first layer | second layer | basis weight ($g/m^2$) |
| NBF 1.5d 100% | NBF 1.5d 40% SH 3d 60% | 25 |

Note:
NBF: a polyethylene/polypropylene composite fiber treated for imparting a hydrophilic nature to the surface thereof (a product of Daiwabo Co., Ltd.)
SH: a polyethylene/polyester composite fiber treated for imparting a hydrophilic nature to the surface thereof (a product of Daiwabo Co., Ltd.)

As is apparent from Examples 1 to 11, the surface material of the present invention is small in the highly viscous liquid absorption time and the amount of returned liquid and excellent in the visual dryness. Particularly, the samples of Examples of 1 to 7 and 9 to 11 exhibited a particularly high level of highly viscous liquid permeability, liquid return preventive effect, and visual dryness and therefore are ideal surface materials.

TABLE 2

| No. | resin | distribution of openings | shape of bottom section | film layer radius of curvature (mm) | size of opening ($mm^2$) | density of opening (per $cm^2$) | slant angle (°) | degree of whiteness (%) |
|---|---|---|---|---|---|---|---|---|
| 1-1 | LLDPE | A-1 | B-1 | 0.52 | 0.22 | 48 | 59 | 42 |
| 1-2 | " | " | " | 1.02 | 0.21 | 50 | 60 | 41 |
| 1-3 | " | " | " | 2.21 | 0.23 | 50 | 58 | 39 |
| 1-4 | " | " | " | 1.09 | 0.09 | 5 | 57 | 61 |
| 1-5 | " | " | " | 1.02 | 0.22 | 137 | 60 | 28 |
| 1-6 | " | " | " | 1.16 | 0.21 | 51 | 31 | 32 |
| 1-7 | " | " | " | 0.98 | 0.21 | 50 | 77 | 59 |
| 1-8 | " | " | " | 1.09 | 0.19 | 52 | 141 | 68 |
| 1-9 | LDPE | " | " | 1.11 | 0.20 | 49 | 62 | 42 |
| 1-10 | EVA | " | " | 1.20 | 0.20 | 48 | 60 | 43 |
| 1-11 | LLDPE | " | B-2 | — | 0.21 | 51 | 59 | 39 |
| 1-12 | " | " | B-3 | — | 0.21 | 51 | 59 | 39 |
| 1-13 | " | A-2 | — | — | 0.20 | 49 | 58 | 17 |

Note:
LLDPE: linear low-density polyethylene (a product of Mitsui Petrochemical Industries, Ltd.)
LDPE: low-density polyethylene (a product of Mitsui Petrochemical Industries, Ltd.)
EVA: ethylene-vinyl acetate copolymer
A-1: all the openings are present in the wall section.
A-2: all the openings are present in the bottom section.
B-1: upward protruding
B-2: flat
B-3: downward protruding

TABLE 3

| | constitution | | performance | | |
|---|---|---|---|---|---|
| | | | highly viscous liquid absorption | amount of liquid return | visual |
| | film layer | fiber layer | time (sec) | (mg) | dryness |
| Ex. 1 | I-1 | presence | 22 | 8 | 4 |
| Ex. 2 | I-2 | " | 30 | 12 | 4 |
| Ex. 3 | I-3 | " | 58 | 15 | 4 |
| Ex. 4 | I-4 | " | 75 | 7 | 4 |
| Ex. 5 | I-5 | " | 27 | 20 | 3 |
| Ex. 6 | I-6 | " | 25 | 21 | 3 |
| Ex. 7 | I-7 | " | 36 | 10 | 4 |
| Ex. 8 | I-8 | " | 125 | 6 | 4 |
| Ex. 9 | I-9 | " | 31 | 10 | 4 |
| Ex. 10 | I-10 | " | 27 | 15 | 4 |
| Ex. 11 | I-2 | absence | 86 | 7 | 4 |

The embodiment (4) of the invention is worked below.

EXAMPLES 1 TO 47

Various surface materials shown in Tables 4 to 7 were prepared by making use of a film layer shown in Tables 1 and 2 and a fiber layer shown in Table 3 as the constituent materials.

Each sample was determined in view of physical properties in the same way as shown before on the average of 10 pieces of the same sample. Klemm absorption is determined below.

The height of the rise of water was measured 10 min after initiation of the water absorption according to JIS-P8141 in the lengthwise direction of the part having an opening region on the surface material of the absorbent article.

TABLE 1

| | | | | | | | | | |
|---|---|---|---|---|---|---|---|---|---|
| | | | | | Film layer (1) | | | | |
| No. | Resin | Size of opening (mm$^2$) | Density of opening (per cm$^2$) | Slant angle (°C.) | Thickness (μm) | TiO$_2$ content (%) | Degree of whiteness (%) | Distribution of openings | Surface treatment |
| I-1 | LLDPE | 0.02 | 48 | 59 | 30 | 15 | 62 | A-1 | B-1 |
| I-2 | " | 0.21 | 50 | 60 | 30 | 15 | 41 | " | " |
| I-3 | " | 5.03 | 50 | 58 | 32 | 15 | 32 | " | " |
| I-4 | " | 0.09 | 5 | 57 | 29 | 15 | 51 | " | " |
| I-5 | " | 0.22 | 138 | 60 | 32 | 15 | 28 | " | " |
| I-6 | " | 0.21 | 51 | 31 | 31 | 15 | 32 | " | " |
| I-7 | " | 0.21 | 50 | 77 | 31 | 15 | 59 | " | " |
| I-8 | " | 0.19 | 52 | 101 | 30 | 15 | 85 | " | " |
| I-9 | " | 0.20 | 49 | 144 | 30 | 15 | 92 | " | " |
| I-10 | " | 0.20 | 48 | 60 | 6 | 14 | 17 | " | " |
| I-11 | " | 0.21 | 51 | 59 | 14 | 15 | 28 | " | " |
| I-12 | " | 0.20 | 49 | 58 | 97 | 15 | 62 | " | " |

Note:
LLDPE: linear low-density polyethylene (a product of Mitsui Petrochemical Industries, Ltd.)
A-1: all the openings are present in the wall section.
B-1: untreated

TABLE 2

| | | | | | Film layer (2) | | | | |
|---|---|---|---|---|---|---|---|---|---|
| No. | Resin | Size of opening (mm$^2$) | Density of opening (per cm$^2$) | Slant angle (°C.) | Thickness (μm) | TiO$_2$ content (%) | Degree of whiteness (%) | Distribution of openings | Surface treatment |
| I-13 | LLDPE | 0.22 | 48 | 61 | 30 | 15 | 34 | A-2 | B-1 |
| I-14 | " | 0.20 | 51 | 59 | 29 | 15 | 28 | A-3 | " |
| I-15 | " | 0.22 | 50 | 58 | 32 | 15 | 12 | A-4 | " |
| I-16 | " | 0.20 | 49 | 61 | 32 | 15 | 40 | A-1 | B-2 |
| I-17 | " | 0.20 | 48 | 59 | 29 | 15 | 39 | " | B-3 |
| I-18 | " | 0.20 | 50 | 60 | 31 | 15 | 42 | " | B-4 |
| I-19 | " | 0.21 | 52 | 62 | 31 | 20 | 52 | " | B-1 |
| I-20 | " | 0.18 | 51 | 58 | 32 | 10 | 29 | " | " |
| I-21 | " | 0.19 | 49 | 61 | 30 | 0 | 5 | " | " |
| I-22 | LDPE | 0.18 | 50 | 60 | 32 | 14 | 39 | " | " |
| I-23 | EVA | 0.20 | 50 | 59 | 31 | 14 | 38 | " | " |
| I-24 | Tafmer | 0.21 | 47 | 58 | 32 | 16 | 41 | " | " |
| I-25 | Blend | 0.20 | 49 | 62 | 29 | 15 | 40 | " | " |

TABLE 2-continued

| | | Film layer (2) | | | | | | | |
|---|---|---|---|---|---|---|---|---|---|
| No. | Resin | Size of opening (mm$^2$) | Density of opening (per cm$^2$) | Slant angle (°C.) | Thickness (μm) | TiO$_2$ content (%) | Degree of whiteness (%) | Distribution of openings | Surface treatment |
| I-26 | LLDPE | 0.22 | 48 | 0 | 30 | 15 | 14 | A-5 | " |

Note:
LDPE: low-density polyethylene (a product of Mitsui Petrochemical Industries, Ltd.)
EVA: ethylene-vinyl acetate copolymer (a product of Mitsui Petrochemical Industries, Ltd.)
Tafmer: ethylene-α-olefin copolymer (a product of Mitsui Petrochemical Industries, Ltd.)
blend: LLDPE-LDPE-Tafmer blend
A-2: the openings are present in the following ratio: the wall/section/the top section = 70/30.
A-3: the openings are present in the following ratio: the wall section/the top section = 30/70.
A-4: all the openings are present in the bottom section.
A-5: openings are present in the flat film.
B-2: a treatment for imparting a hydrophilic nature was conducted by application of a surfactant (Pelex OTP; a product of Kao Corp.)
B-3: a treatment for imparting a hydrophilic nature was conducted by plasma radiation in an argon gas atmosphere.
B-4: a treatment for imparting a hydrophobic nature was conducted by application of a fluorinated repellent (Bosui; a product of Sony Chemical Corp.)

TABLE 3

| | | Fiber layer | | | | | | | |
|---|---|---|---|---|---|---|---|---|---|
| | | Composition | | | | | | Treatment | Weight per unit area (g/m$^2$) |
| | Kind | 1st layer | | | 2nd layer | | | Kind | Deposition (%) | |
| II-1 | dry heat-bonded nonwoven fabric | ESHB ES | 3d 1.5d | 40% 60% | ESHB ES | 3d 3d | 65% 35% | C-1 | 0.34 | 11 |
| II-2 | dry heat-bonded nonwoven fabric | ESHB ES | 3d 1.5d | 40% 60% | ESHB ES | 3d 3d | 65% 35% | " | 1.02 | 25 |
| II-3 | dry heat-bonded nonwoven fabric | ESHB ES | 3d 1.5d | 40% 60% | ESHB ES | 3d 3d | 65% 35% | " | 0.35 | 25 |
| II-4 | dry heat-bonded nonwoven fabric | ESHB ES | 3d 1.5d | 40% 60% | ESHB ES | 3d 3d | 65% 35% | " | 0.09 | 25 |
| II-5 | dry heat-bonded nonwoven fabric | ESHB ES | 3d 1.5d | 40% 60% | ESHB ES | 3d 3d | 65% 35% | free | — | 25 |
| II-6 | dry heat-bonded nonwoven fabric | ESHB ES | 3d 1.5d | 40% 60% | ESHB ES | 3d 3d | 65% 35% | C-2 | 0.35 | 25 |
| II-7 | dry heat-bonded nonwoven fabric | ESHB ES | 3d 1.5d | 40% 60% | ESHB ES | 3d 3d | 65% 35% | C-1 | 0.33 | 40 |
| II-8 | dry heat-bonded nonwoven fabric | Es | 1.5d | 100% | SH ES | 3d 1.5d | 60% 40% | " | 0.36 | 25 |
| II-9 | dry heat-bonded nonwoven fabric | ES | 2d | 100% | SH | 2d | 100% | " | 0.34 | 20 |
| II-10 | dry heat-bonded nonwoven fabric | ES SH | 2d 2d | 40% 60% | ES ES | 2d 2d | 35% 65 | " | 0.35 | 26 |
| II-11 | dry heat-bonded nonwoven fabric | ES SH | 2d 2d | 40% 60% | ES ES | 2d 2d | 35% 65% | " | 5.35 | 26 |
| II-12 | dry heat-bonded nonwoven fabric | ES | 1.5d | 100% | | | | C-1 | 0.32 | 25 |
| II-13 | high-pressure fluid-inter-laced nonwoven fabric | ES PET | 2d 2d | 50% 50% | | | | " | 0.33 | 30 |
| II-14 | spun-bonded nonwoven fabric | | | | polyester | | | absent | — | 20 |
| II-15 | spun-bonded nonwoven fabric | | | | rayon | | | C-3 | 1.51 | 28 |
| II-16 | dry-binder nonwoven fabric | | | | " | | | " | 1.33 | 40 |
| II-17 | wet nonwoven fabric | | | | " | | | " | 1.87 | 30 |
| II-18 | paper | | | | kraft pulp | | | " | 1.56 | 33 |
| II-19 | " | | | | " | | | absent | — | 33 |
| II-20 | web | | | | " | | | C-3 | 1.28 | 21 |
| II-21 | " | | | | " | | | absent | 1.28 | 21 |
| II-22 | " | Ray | 3d | 100% | | | | C-3 | 1.83 | 15 |

TABLE 3-continued

| | | Fiber layer | | | | Weight per |
|---|---|---|---|---|---|---|
| | | Composition | | | Treatment | unit area |
| | | | | | Deposition | |
| Kind | | 1st layer | | 2nd layer | Kind (%) | (g/m²) |
| II-23 | " | PET | 2d | 100% | C-1 0.31 | 20 |

Note:
II-1 to II-12: a predetermined fiber was formed into a web with a miniature card, followed by hot-air treatment.
II-13: a predetermined fiber was formed into a web with a miniature card, followed by high-pressure water stream treatment.
II-14: "Aiel"; a product of Asahi Chemical Industry Co., Ltd.
II-15: "Taiko TCF"; a product of Futamura Chemical Industries Co., Ltd.
II-16: "Counter Cloth"; a product of Kuraflex.
II-17: "Vx"; a product of Inogami Co., Ltd.
II-18 and II-19: a product of Inogami Co., Ltd.
II-20 and II-21: a pulp was formed into a web by the air-lay method.
II-22 and II-23: a predetermined fiber was formed into a web with a miniature card.
ES: polyethylene/polypropylene composite fiber (a product of Chisso Corporation)
ESHB: polyethylene/polypropylene composite fiber (a product of Chisso Corporation)
SH: polyethylene/polyester composite fiber (a product of Daiwabo Co., Ltd.)
PET: polyester fiber (a product of Teijin Limited)
Ray: rayon fibe (a product of Daiwabo Co., Ltd.)
C-1: a mixed system comprising an alkyl phosphate and a sorbitan fatty acid ester
C-2: silicone treatment
C-3: alkyl ketene dimer treatment

TABLE 4

Constitution and performance of surface material (1)

| | Constitution | | | Klemm water | Performance | | | |
|---|---|---|---|---|---|---|---|---|
| | Film layer | Fiber layer | Integration method | absorption (mm) | Absorption time (sec) | Amount of returned liquid (mg) | Hand and drape (grade) | Visual dryness |
| Ex. 1 | I-1 | II-3 | C-1 | 29 | 26 | 4 | 3 | 4 |
| Ex. 2 | I-2 | " | " | 31 | 18 | 9 | 3 | 4 |
| Ex. 3 | I-3 | " | " | 30 | 4 | 22 | 3 | 4 |
| Ex. 4 | I-4 | " | " | 32 | 37 | 6 | 3 | 4 |
| Ex. 5 | I-5 | " | " | 30 | 6 | 31 | 3 | 4 |
| Ex. 6 | I-6 | " | " | 30 | 14 | 24 | 3 | 4 |
| Ex. 7 | I-7 | " | " | 30 | 28 | 5 | 3 | 4 |
| Ex. 8 | I-8 | " | " | 31 | 52 | 8 | 3 | 4 |
| Ex. 9 | I-9 | " | " | 29 | 69 | 6 | 3 | 4 |
| Ex. 10 | I-10 | " | " | 29 | 44 | 15 | 3 | 4 |
| Ex. 11 | I-11 | " | " | 32 | 18 | 6 | 3 | 4 |

Note:
C-1: a resin film was laminated on fiber layer, followed by formation of an opening region having a shape shown in FIG. 2 with an embossing roller.

TABLE 5

Constitution and performance of surface material (2)

| | Constitution | | | Klemm water | Performance | | | |
|---|---|---|---|---|---|---|---|---|
| | Film layer | Fiber layer | Integration method | absorption (mm) | Absorption time (sec) | Amount of returned liquid (mg) | Hand and drape (grade) | Visual dryness |
| Ex. 12 | I-13 | II-3 | C-1 | 32 | 26 | 51 | 3 | 3 |
| Ex. 13 | I-14 | " | " | 31 | 21 | 70 | 3 | 3 |
| Ex. 14 | I-15 | " | " | 33 | 18 | 87 | 3 | 2 |
| Ex. 15 | I-16 | " | " | 28 | 12 | 18 | 3 | 4 |
| Ex. 16 | I-17 | " | " | 27 | 13 | 17 | 3 | 4 |
| Ex. 17 | I-18 | " | " | 29 | 37 | 6 | 3 | 4 |
| Ex. 18 | I-19 | " | " | 30 | 30 | 11 | 3 | 4 |
| Ex. 19 | I-20 | " | " | 31 | 28 | 12 | 3 | 3 |
| Ex. 20 | I-22 | " | " | 29 | 29 | 8 | 3 | 4 |
| Ex. 21 | I-23 | " | " | 29 | 32 | 9 | 3 | 4 |
| Ex. 22 | I-24 | " | " | 32 | 28 | 7 | 3 | 4 |
| Ex. 23 | I-25 | " | " | 31 | 31 | 10 | 3 | 4 |
| Ex. 24 | I-26 | " | " | 29 | 32 | 86 | 3 | 2 |

TABLE 6

Constitution and performance of surface material (3)

| | Constitution | | | Klemm water | Performance | | | |
|---|---|---|---|---|---|---|---|---|
| | Film layer | Fiber layer | Integration method | absorption (mm) | Absorption time (sec) | Amount of returned liquid (mg) | Hand and drape (grade) | Visual dryness |
| Ex. 25 | I-2 | II-1 | C-1 | 26 | 34 | 15 | 3 | 4 |
| Ex. 26 | " | II-2 | " | 37 | 13 | 17 | 3 | 3 |
| Ex. 27 | " | II-4 | " | 8 | 45 | 9 | 3 | 4 |

TABLE 6-continued

Constitution and performance of surface material (3)

| | Constitution | | | Klemm water absorption (mm) | Performance | | | |
|---|---|---|---|---|---|---|---|---|
| | Film layer | Fiber layer | Integration method | | Absorption time (sec) | Amount of returned liquid (mg) | Hand and drape (grade) | Visual dryness |
| Ex. 28 | " | II-5 | " | 0 | 49 | 6 | 3 | 4 |
| Ex. 29 | " | II-6 | " | 0 | 54 | 3 | 3 | 4 |
| Ex. 30 | " | II-7 | " | 29 | 20 | 7 | 3 | 4 |
| Ex. 31 | " | II-8 | " | 50 | 11 | 10 | 3 | 4 |
| Ex. 32 | " | II-9 | " | 30 | 14 | 12 | 3 | 4 |
| Ex. 33 | " | II-10 | " | 29 | 13 | 11 | 3 | 4 |
| Ex. 34 | " | II-12 | " | 33 | 14 | 14 | 3 | 4 |
| Ex. 35 | " | II-13 | " | 52 | 26 | 77 | 3 | 3 |
| Ex. 36 | " | II-14 | " | 0 | 72 | 25 | 3 | 2 |
| Ex. 37 | " | II-15 | " | 75 | 23 | 72 | 2 | 2 |
| Ex. 38 | " | II-16 | " | 89 | 37 | 73 | 2 | 2 |
| Ex. 39 | " | II-17 | " | 78 | 38 | 86 | 2 | 2 |
| Ex. 40 | " | II-18 | " | 76 | 29 | 88 | 2 | 2 |

TABLE 7

Constitution and performance of surface material (4)

| | Constitution | | | Klemm water absorption (mm) | Performance | | | |
|---|---|---|---|---|---|---|---|---|
| | Film layer | Fiber layer | Integration method | | Absorption time (sec) | Amount of returned liquid (mg) | Hand and drape (grade) | Visual dryness |
| Ex. 41 | I-2 | II-20 | C-2 | 58 | 80 | 83 | 2 | 2 |
| Ex. 42 | " | II-22 | " | 45 | 78 | 67 | 2 | 2 |
| Ex. 43 | " | II-23 | " | 19 | 89 | 64 | 3 | 3 |
| Ex. 44 | I-6 | II-8 | C-1 | 28 | 11 | 24 | 3 | 4 |
| Ex. 45 | " | II-9 | " | 30 | 12 | 26 | 3 | 4 |
| Ex. 46 | I-7 | II-8 | " | 31 | 25 | 6 | 3 | 4 |
| Ex. 47 | " | II-9 | " | 29 | 27 | 8 | 3 | 4 |

Note:
C-2: a film layer alone was treated with an embossing roller to form an opening region having a shape shown in FIG. 2, followed by fixation of a fiber layer thereon by means of heat bonding.

As can be seen from Examples 1 to 47, the surface material of the present invention is small in the absorption time and the amount of returned liquid and excellent in the visual dryness as well as in the hand and drape. Particularly, the samples of Examples 1 to 7, 10, 11, 15 to 34 and 44 to 47 exhibited a remarkably high level of liquid return preventive effect and visual dryness and therefore are ideal surface materials.

We claim:

1. A sanitary article comprising:
an absorbent; and
a sheet of surface material enveloping said absorbent, said sheet including an opaque, hydrophobic film, said film having an inner surface and an outer surface, said inner surface being disposed in a facing relationship toward said absorbent, and a layer of fibrous aggregates, said layer enveloping said film and having a first surface and a second surface, said first surface being affixed to said outer surface, said sheet further including a top section having recess portions extending toward said absorbent, each said recess portion having a bottom section and a wall section, said wall section linking said top section and said bottom section and having at least one wall portion inclined to said top section, each said inclined wall portion being provided with at least one opening.

2. The sanitary article as claimed in claim 1, wherein an angle formed between said top section and said inclined portion is in the range of from 20° to less than the right angle.

3. The sanitary article as claimed in claim 1, wherein said sheet of surface material has an extent of deformation at the thickness direction of 40 percent or greater at a pressure of 50 grams per square cm.

4. The sanitary article as claimed in claim 3, wherein each said opening has an area of 0.02 to 30 square mm and the number of openings ranges from 1 to 100 per one square cm of said sheet of surface material.

5. A sanitary article comprising:
an absorbent; and
a sheet of surface material enveloping said absorbent, said sheet including an opaque, hydrophobic film, said film having an inner surface and an outer surface, and a layer of fibrous aggregates, said layer having a first surface and a second surface, said first surface being affixed to said inner surface, said second surface being disposed in a facing relationship toward said absorbent, said sheet further including a top section, said top section having recess portions extending toward said absorbent, each said recess portion having a bottom section and a wall section, said wall section linking said top section and said bottom section and having at least one wall portion inclined to said top section, each said inclined wall portion being provided with at least one opening.

6. A sanitary article as claimed in claim 5, wherein said bottom is formed upwardly convex.

7. The sanitary article as claimed in claim 5, wherein the integral structure of said sheet of surface material has a Klemm's method of water absorption value of height of the rise of water, as determined in JIS P8141, of 100 mm or lower.

8. The sanitary article as claimed in claim 5, wherein said sheet of surface material has an extent of deformation at the thickness direction of 40 percent or greater at a pressure of 50 grams per square cm.

9. The sanitary article as claimed in claim 8, wherein each said opening has an area of 0.02 to 30 square mm and the number of openings ranges from 1 to 100 per one square cm of said sheet of surface material.

10. The sanitary article as claimed in claim 5, wherein an angle formed between said top section and said inclined portion is in the range of from 20° to less than the right angle.

* * * * *